United States Patent
Sommermeyer

(10) Patent No.: US 7,393,841 B2
(45) Date of Patent: Jul. 1, 2008

(54) HYPERBRANCHED AMYLOPECTIN FOR USE IN METHODS FOR SURGICAL OR THERAPEUTIC TREATMENT OF MAMMALS OR IN DIAGNOSTIC METHODS, ESPECIALLY FOR USE AS A PLASMA VOLUME EXPANDER

(75) Inventor: Klaus Sommermeyer, Rosbach v.d.H (DE)

(73) Assignee: Supramol Parenteral Colloids GmbH, Rosbach V.D.H. (DE)

( * ) Notice: Subject to any disclaimer, the term of this patent is extended or adjusted under 35 U.S.C. 154(b) by 468 days.

(21) Appl. No.: 10/486,943

(22) PCT Filed: Aug. 6, 2002

(86) PCT No.: PCT/EP02/08757

§ 371 (c)(1),
(2), (4) Date: Feb. 13, 2004

(87) PCT Pub. No.: WO03/018639

PCT Pub. Date: Mar. 6, 2003

(65) Prior Publication Data

US 2004/0157207 A1    Aug. 12, 2004

(30) Foreign Application Priority Data

Aug. 22, 2001    (DE) ................. 101 41 099

(51) Int. Cl.
*A61K 31/718*    (2006.01)
(52) U.S. Cl. ................. 514/60; 514/54; 536/2
(58) Field of Classification Search ........... 514/54, 514/60; 536/2
See application file for complete search history.

(56) References Cited

U.S. PATENT DOCUMENTS

| | | | |
|---|---|---|---|
| 4,111,199 A * | 9/1978 | Djerassi ................ | 604/6.02 |
| 4,125,492 A | 11/1978 | Cuatrecasas et al. | |
| 4,454,161 A * | 6/1984 | Okada et al. .......... | 426/48 |
| 4,629,698 A | 12/1986 | Nitsch et al. | |

FOREIGN PATENT DOCUMENTS

| | | |
|---|---|---|
| DE | 3029307 | 3/1982 |
| DE | 19628705 | 1/1998 |
| DE | 10112825 | 10/2002 |
| EP | 0418523 A1 | 3/1991 |
| EP | 0418523 B1 | 3/1991 |
| EP | 418945 A1 * | 3/1991 |
| EP | 1 075 839 A1 | 2/2001 |
| GB | 1 279 356 A | 6/1972 |
| WO | WO 00 18893 | 4/2000 |

OTHER PUBLICATIONS

The Merck Index, 12th edition. Budavari, S. et al., Eds. Merck & Co.: Whitehouse Station, NJ. 1996. Entry 4506 (Glycogen), pp. 765-766.*

Database Chemabs 'Online!, Chemical Abstracts Service, Columbus, Ohio, US;, "Manufacture of Highly-Branched Starch inhibition of Retrogradation of Starch, and Food Containing the Starch," retrieved from STN, Accession No. 135:317549, XP 002222974, Zusammenfassung & JP 2001 294601 A, Oct. 23, 2001.

Gunja ,Zeenat H., et al., "Enzymic Conversion of Amylopectin into a Glycogen-type Polysaccharide," Chemistry & Industry., p. 1017 (1959).

* cited by examiner

*Primary Examiner*—L Blaine Lankford
*Assistant Examiner*—Susan E. Fernandez
(74) *Attorney, Agent, or Firm*—Hamilton, Brook, Smith & Reynolds, P.C.

(57) ABSTRACT

The invention relates to the use of hyperbranched amylopectin which has an average branch degree of between >10 and 25 mol % and a molecular weight (Mw) ranging from 40.000-800.000 Dalton and the derivatives thereof in methods for surgical or therapeutic treatment of human or animal bodies or in a diagnostic method, preferably as a plasma volume expander. Plasma volume expanders based on hydroxy-ethylated amylopectin have, as a result of hydroxy ethylation, hitherto exhibited the disadvantage of incomplete metabolism and thus temporary tissue storage which is linked to side-effects. According to the invention, novel plasma expanders based on polysaccharides which do not exhibit the same disadvantages as the former are provided. Improved, completely metabolised plasma expanders based on hyperbranched amylopectin which can be obtained therefrom so that native plant-amylopectins are altered-by transglycosylation in such a way the adjustable, high degree of branching enables control of the serum-α-amylase decomposition so that no or only a very insignificant degree of hydroxy ethylation is necessary.

9 Claims, No Drawings

HYPERBRANCHED AMYLOPECTIN FOR USE IN METHODS FOR SURGICAL OR THERAPEUTIC TREATMENT OF MAMMALS OR IN DIAGNOSTIC METHODS, ESPECIALLY FOR USE AS A PLASMA VOLUME EXPANDER

RELATED APPLICATIONS

This application is the U.S. National Stage of International Application No. PCT/EP02/08757, filed Aug. 6, 2002, and published in German, which claims the benefit of German Application No. 101 41 099.9, filed Aug. 22, 2001.

The present invention relates to the use of hyperbranched amylopectin.

In particular, the invention relates to a novel use of hyperbranched amylopectin which exhibits a specific degree of branching and a specific molecular weight Mw.

In the course of the history of the development of plasma volume expanders, it has always been one of the aims to achieve the globular structure of the natural carrier of the colloidal-osmotic pressure in the serum, namely albumin. Glycogen, which also occurs as a natural retention polysaccharide in the human organism, comes closest to this globular structure. Glycogen achieves its globular structure as a result of its very high degree of branching. From the structural point of view, glycogen is a glucose polysaccharide with α-1,4 glycosidic bonds, in linear sections, to which α-1,6 glycosidic branch points are fixed. Because glycogen itself is not available as a cheap raw material source, Wiedersheim suggested in 1957 to use instead less branched amylopectin as a starting material for the production of the plasma expander hydroxyethyl starch (HES). In the meantime, hydroxyethyl starch is being used in the form of several different types on a very wide scale as plasma expander. This development has led to new types of hydroxethyl starch types (HES types) which exhibit an optimum volume effect with otherwise minimal side effects such as e.g. influencing clotting or intermediate retention in the tissue.

The various types of HES present on the market differed regarding their molecular weight, average degree of substitution and substitution pattern.

In spite of the substantial progress achieved by way of these developments, some disadvantages have remained even in the case of the HES types optimised in the last few years, particularly the inability of being completely metabolised.

It is well known, however, that chemically speaking, the hydroxyethyl ether group is metabolically extremely stable so that those anhydroglucoseunits of hydroxyethyl starch which carry hydroxyethyl ether groups are practically impossible to metabolise. Moreover, it is known that only those α-1,4 glycosidic bonds in the hydroxyethyl starch molecule can be split by serum (x-amylase which are formed by non-substituted glucose units. For this reason, it has been found that even in the case of the optimized types of HESa minimal but yet still remarkablehistoretention can be ascertained at least over certain periods of time.

As a further disadvantage, it has been found that HES does not possess the ideal globular structure of albumin and its intrinsic viscosity is therefore considerably higher than that of albumin. A relatively low viscosity is desirable in the case of a plasma expander because, following its application in the circulation, the total blood viscosity would be influenced in the sense of a reduction.

The task therefore existed of developing new improved plasma expanders based on amylopectin which do not exhibit the disadvantages of a lack of complete metabolisability of the amylopectin derivative hydroxyethyl starch. At the same time, the new plasma expander was to have a more globular structure and to be thus capable of forming relatively low viscosity solutions.

It can also be considered to be one of the tasks of the invention to open up further fields of application for certain amylopectins.

These tasks as well as further tasks not listed in detail which, however, can be derived freely and easily from the introductory explanations are achieved by the subject matter of claims 1. Preferred embodiments of the invention are the subject matter of the claims which refer back to claim 1.

By using hyperbranchedamylopectin with an average degree of branching of between >10 and 25 mole % and an average molecular weight Mw in the region of 40,000 to 800,000 Dalton and, if necessary, its derivatives in methods for the surgical or therapeutic treatment of the human or animal body (including that of mammals) or in diagnostic methods it is possible to open up, in a not directly foreseeable manner, on the one hand a number of new and interesting applications in the medical field for hyperbranchedamylopectin. On the other hand, an almost ideal substitute for the starch-based HES products still commonly used in practice at present is provided specifically with respect to the 'plasma volume expansion' sector, leading to far fewer dangerous side effects.

With respect to plasma volume expansion, it has in fact been found in connection with the invention as a result of extensive studies and investigations that the residual fractions of hydroxyethyl starch in the blood stream and in urine exhibit a strong increase in the degree of branching a few hours or even days after the application of a plasma expander in comparison with the originally infused hydroxyethyl starch (HES product). The degrees of branching, expressed in mole % of the anhydroglucoses carrying branch points thus increased from approx. 5 mole % to more than 7 mole % 2 hours after application and to 8 mole % 7 hours after application. At the same time, an even higher degree of branching of 9 or 10 mole % became apparent in the overall urine fraction 48 or 42 hours after infusion. This phenomenon was observed irrespective of the molecular weight, the degree of substitution or the substitution pattern of the hydroxyethyl starch applied. This means that, when breaking down, these fractions increasingly acquire a structure and/or branching approaching that resembling glycogen, which is indicated in the literature as being branching at a level as high as approx. 10 mole %.

Surprisingly enough, it has now been found that the relative stability of α-(1,6) branching in amylopectin and in derivatives thereof can be exploited to reduce the breakdown of amylopectin in comparison with the dominant α-amylase breakdown to such an extent that a polysaccharide capable of breaking down completely can be produced which, however, still exhibits the properties of an ideal plasma expander as regards the pharmacokinetics and/or the volume effect.

Consequently, the invention comprises the use of hyperbranchedamylopectins and of derivatives of such hyperbranchedamylopectins in the medical sector.

The term amylopectin should be understood to mean in general first of all branched starches or starch products with α-(1,4) and α-(1,6) bonds between the glucose molecules. These ramifications of the chain take place via the α-(1,6) bonds. In the case of naturally occurring amylopectins these occur in an irregular manner approx. every 15-30 glucose segments. The molecular weight of naturally occurring amylopectin is very high, i.e. in the region of $10^7$ to $2\times10^8$ Dalton. It is assumed that amylopectin, too, forms helices within certain limits.

It is possible to define a degree of branching for amylopectins. The ratio of the number of anhydroglucose molecules carrying branch points (α-(1,6) bonds) to the total number of anhydroclucose molecules of amylopectin is a measure of branching, this ratio being expressed in mole. Naturally occurring amylopectin has a degree of branching of approx. 4 mole %. However, it is known that, when considered in isolation, clusters and molecule sections of amylopectin exhibit a slightly higher degree of branching compared with the natural average degree of branching.

Hyperbranchedamylopectins according to the meaning of the invention are those amylopectins which exhibit a degree of branching which significantly exceeds the degree of branching known for amylopectin from nature. The degree of branching is, in any case, an average value (average degree of branching) since amylopectins are polydisperse substances.

Such hyperbranchedamylopectins exhibit significantly higher degrees of branching, expressed in mole % of branching anhydroglucoses, in comparison with unchanged amylopectin or hydroxyethyl starch and consequently resemble glycogen more closely in terms of their structure.

The average degree of branching of hyperbranchedamylopectin necessary for the application according to the invention is in the region between >10 and 25 mole %. This means that amylopectins useful according to the meaning of the invention exhibit on average an α-(1,6) bond and consequently a branch point approximately every 10 to 14 glucose units. If the degree of branching is below 10 mole %, the breakdown of branched amylopectin is insufficiently retarded (e.g. in the case of its use as a plasma expander). If the degree of branching is more than 25 mole %, the breakdown is excessively delayed such that its use-as a plasma volume expander, for example is precluded.

A type of amylopectin that can preferably be used in the medical field is characterised by a degree of branching of between 11 and 16 mole %.

Other preferred hyperbranchedamylopectins exhibit a degree of branching in the region of between 13 and 16 mole %.

In addition, the molecular weight Mw of hyperbranchedamylopectin is also important. The molecular weight Mw indicates the weight average of the molecular weight as is measurable by relevant methods providing this average value. These include aqueous GPC, HPLC, light scattering and such like.

The hyperbranchedamylopectins suitable for use according to the invention generally exhibit a value for the weight average of the molecular weight of 40,000 to 800,000 Dalton. The lower limit value for the molecular weight range Mw is obtained in the case of the preferred applications essentially from the so-called 'renal threshold' which must be set at approx. 40,000 in the case of the hyperbranched compounds. If Mw is less than 40,000 Dalton, the molecules would be filtered off too rapidly via the kidneys. Above a Mw of 800,000 Dalton, no additional usefulness worth mentioning would be achieved even though the limit viscosity no longer depends on the molecular weight in the case of a globular structure.

Average values Mw of between 90,000 and 300,000 Dalton are preferred for use as plasma volume expanders, with molecular weights Mw of between 120,000 and 250,000 Dalton being particularly appropriate.

A particular embodiment of the invention comprises hyperbranchedamylopectin, the average degree of branching being between 11 and 16 mole % and the molecular weight Mw being between 90,000 and 300,000 Dalton. Other appropriate embodiments of the invention include a hyperbranchedamylopectin, the average degree of branching being between 13 and 16 mole % and the molecular weight Mw being between 120,000 and 250,000 Dalton.

The above-mentioned parameters, namely the degree of branching and the molecular weight, allow a targeted effect being exerted and thus desired pharmacokinetics being set, in particular a desired x-amylase breakdown being achieved. The degree of branching of amylopectin has a key role to play in this connection. However, the molecular weight, too, influences the kinetics concerned. Moreover, it may also be possible to influence the kinetics of amylopectin breakdown to take a desired direction by varying the distribution of the branch points.

Of particular importance for breaking down amylopectin by α-amylase and consequently for the operation of the plasma volume expander, however, is the degree of branching. As a result of the high degree of branching, the attack of α-amylase is greatly delayed and in areas of the molecule with a high density of the branch points altogether eliminated since no access of ?-amylase is possible there. Such compounds are nevertheless capable of breaking down by other enzymes down to oligosaccharides and finally glucose.

If need be, hyperbranchedamylopectins to be used according to the invention can be obtained in the form of derivatives. Such derivatives comprise chemical derivatives of amylopectin such as e.g. those obtainable by chemical or biotechnology conversions.

Preferred derivatives of hyperbranchedamylopectin are hydroxyethylamylopectin, hydroxypropyl amylopectin and acetyl amylopectin. Of these, hydroxyethylamylopectin in turn is particularly advantageous to use. The kinetics of amylopectin breakdown can consequently also be influenced byderivatisation. However, it is advantageous for the degree of derivatisation, e.g. the degree of hydroxyethylation to be considerably lower in these cases in order to achieve a comparable volume effect or similar pharmacokinetics in comparison with hydroxyethyl starch (HES) produced from normally branched amylopectin.

The production of hyperbranchedamylopectin which is suitable according to the meaning of the invention—among other things and preferably—for use as a plasma volume expander takes place in a manner known as such by enzymatic conversion by so-called branching enzymes which catalyse the hydrolysis of α1,4 glycosidic bonds and their conversion to α-1,6 glycosidic compounds. Such so-called transfer enzymes can be extracted in the known way e.g. from algae according to PCT WO 0018893. However, from U.S. Pat. No. 4,454,161 and EP 0418945, other glycogen branching enzymes are known which can also be used correspondingly. The execution of enzymatic transglycosilation takes place in a manner known as such e.g. by the incubation of waxy maize starch with the corresponding enzymes under mild conditions at a pH around approx. 7,5 and temperatures of approx. 30° C. in aqueous solution. Working up of the reaction preparation takes place subsequently again in the known way, the enzymes having been first deactivated or removed by changing the pH or by filtration steps.

In a subsequent hydrolysis step which preferably takes place by means of hydrochloric acid, the desired molecular weight of the product is adjusted. By diafiltration with membranes with a cut off of approx. 3,000 Dalton, the product is subsequently freed from low molecular compounds and common salt formed during the neutralization of the acidic hydrolysis preparation. The product is isolated e.g. by spray drying.

Apart from being used as plasma volume expander, hyperbranchedamylopectins can also be usefully employed in other areas of medicine. Hyperbranchedamylopectin can thus be used for all those applications in the field of therapy and surgery in which standard HES products based on normally branched types of starch can be used.

Apart from the use as plasma volume expander, this involves preferably the use for the improvement of microcirculation, the use as sedimentation aid in cell separation in connection with leucapheresis or the use for cryo-conservation of blood components such as erythrocytes or granulocytes.

MODEL EXAMPLE 1

Comparative Breakdown Tests With Differently Branched α-1-4/α-1-6 Glucosaccharides Glycogen from oysters from SIGMA was broken down by thermoresistant α-amylse BAN 480 L from NOVOZYMES in a mixture of DMSO and water with a 30% content of DMSO at 70° C. and a pH of 6.0. The course of the reaction was monitored by measuring the changes in the molecular weight by gas chromatography and the reaction was stopped after approx. 2 hours by the addition of caustic soda solution for enzyme activation. After neutralization, the product was fractionated by ultrafiltration by means of a cellulose acetate ultrafilter with a nominal cut-off of 1,000 D and 25,000 D for the removal of low molecular fractions and remaining high molecular fractions. The product was subsequently treated with the ion exchanger Amberlite IR 200 C and activated carbon, precipitated with ethanol and dried at 80° C.

The degree of branching determined by $^1$H NMR spectroscopy (integration of the signals of anomeric protons) gave a degree of branching of 15 mole %. The average molecular weight Mw was 7,000 Dalton.

Thin boiling waxy maize starch (≧95% amylopectin) (Cerestar) was treated in the same way as described above. The isolated, highly branched fraction of the branching cluster exhibited a degree of branching of 11 mole %, the average molecular weight Mw was 8,000 Dalton.

The highly branched cluster fractions of amylopectin and glycogen were subsequently subjected to a breakdown test by means of porcine pancreas α-amylase (Roche) in phosphate buffer at pH 7.2 in a 1% solution at 37° C. and with 0,5 IU/ml enzyme and the breakdown kinetics were monitored by measuring the changes in molecular weight by gel chromatography. A comparative test of the breakdown by means of commercial hydroxyethyl starch plasma volume expander was also carried out (Voluven, Fresenius Kabi). Clear differences in the breakdown kinetics were obtained. The half-life of the molecular weight (reduction of the average molecular weight Mw of the starting substance to half the initial value) was 60 minutes in the case of the fraction with a degree of branching of 15% and consequently reached the half-life determined under the same test conditions as that of the Voluven plasma expander.

The half-life for the fraction with an average degree of branching of 11 mole %, on the other hand, was only 25 minutes and it was thus considerably shorter.

MODEL EXAMPLE 2

Thin boiling waxy maize starch from Cerestar with an average degree of branching determined by NMR of 4 mole % was subjected to a breakdown test by porcine pancreas (x-amylase according to the data given in example 1. For this purpose, a 1% solution was gelatinised in phosphate buffer at pH 7.2 by brief heating to approx. 90° C. and, after cooling, the enzyme was added to the preparation in a quantity resulting in 0,5 IU per ml.

The test temperature was 37° C.

The breakdown kinetics were monitored by determining the changes in the molecular weight by gel chromatography. The molecular weight of the starting substance was reduced to half the value within 10 minutes under the same conditions as in example 1.

In comparison with the hyperbranched α-1-4/α-1-6 glucosaccharides from example 1, the on average relative low-branched, thin boiling waxy maize starch is thus broken down by α-amylase so rapidly that it would not be usable as plasma expander.

In this way, the two model examples 1 and 2 demonstrate that even if the molecular weights are low, higher levels of branching lead to a delay in the breakdown of α-amylase and that this effect can be used for the manufacture of a plasma expander.

The invention claimed is:

1. A hyperbranched amylopectin which exhibits an average degree of branching, expressed in mole % of the anhydroglucoses carrying branch points, of between greater than 10 and 25 mole % and a weight average of the molecular weight Mw in the region of 40,000 to 800,000 Dalton.

2. A plasma volume expander comprising the hyperbranched amylopectin according to claim 1.

3. The hyperbranched amylopectin according to claim 1, the average degree of branching being between 11 and 16 mole % and the weight average of the molecular weight Mw between 90,000 and 300,000 Dalton.

4. The hyperbranched amylopectin according to claim 1, the average degree of branching being between 13 and 16 mole % and the weight average of the molecular weight Mw between 120,000 and 250,000 Dalton.

5. A method of separation of blood cells during leukopheresis, comprising adding hyperbranched amylopectin of claim 1 to blood, thereby causing sedimentation of at least one type of blood cells.

6. A method of cryo-conservation of blood components selected from erythrocytes and granulocytes, comprising adding to blood components being conserved hyperbranched amylopectin of claim 1.

7. A hyperbranched hydroxyethyl amylopectin, hydroxypropyl amylopectin, or acetyl amylopectin, which exhibits an average degree of branching, expressed in mole % of the anhydroglucoses carrying branch points, of between greater than about 10 and 25 mole % and a weight average of the molecular weight Mw in the region of 40,000 to 800,000 Dalton.

8. A method of treating a human or animal in need of treatment with a plasma volume expander, comprising administering the hyperbranched amylopectin of claim 1 to the human or animal.

9. A method of treating a human or animal in need of treatment to improve microcirculation, comprising administering the hyperbranched amylopectin of claim 1 to the human or animal.

* * * * *